(12) United States Patent
Larik et al.

(10) Patent No.: US 6,746,481 B1
(45) Date of Patent: Jun. 8, 2004

(54) IMPLATABLE DEVICE INCLUDING A POLYAMINO ACID COMPONENT

(75) Inventors: Vincent Larik, Kerkrade (NL); Marc Hendriks, Brunssum (NL); Michel Verhoeven, Maastricht (NL); Patrick Cahalan, Windham, NH (US); Linda Cahalan, Windham, NH (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/340,440

(22) Filed: Jun. 28, 1999

(51) Int. Cl.[7] .................................................. A61F 2/06
(52) U.S. Cl. ................................................... 623/1.45
(58) Field of Search ................................ 606/194, 198, 606/108, 192, 195; 623/1.15, 1.13, 1.12, 1.44, 1.45, 1.46

(56) References Cited

U.S. PATENT DOCUMENTS

| 5,282,823 | A | * | 2/1994 | Schwartz et al. | 606/198 |
|---|---|---|---|---|---|
| 5,554,180 | A | * | 9/1996 | Turk | 606/194 |
| 5,591,227 | A | | 1/1997 | Dinh et al. | 623/1 |
| 5,628,785 | A | | 5/1997 | Schwartz et al. | 623/1 |
| 5,634,895 | A | | 6/1997 | Igo et al. | 604/21 |
| 5,660,873 | A | | 8/1997 | Nikolaychik et al. | 427/2.24 |
| 5,827,512 | A | * | 10/1998 | Gleich | 424/78.05 |

* cited by examiner

Primary Examiner—Kevin T. Truong
(74) Attorney, Agent, or Firm—Girma Wolde-Michael; Michael C. Soldner

(57) ABSTRACT

An implantable device for reducing restenosis includes a structure including a polyamino acid component, wherein the polyamino acid component can be in the form of a coating or a film on the structure or it can be an integral part of the structure.

20 Claims, 1 Drawing Sheet

US 6,746,481 B1

IMPLATABLE DEVICE INCLUDING A POLYAMINO ACID COMPONENT

FIELD OF THE INVENTION

This invention relates to an implantable device including polyamino acid(s), wherein the polyamino acid(s) can form a coating or film on the device or the device itself can be formed from polyamino acid(s).

RELATED ART

Stenosis is a narrowing or constriction of a duct or canal. A variety of disease processes, such as atherosclerotic lesions, immunological reactions, congenital abnormalities, and the like, can lead to stenosis of arteries or ducts. In the case of stenosis of a coronary artery, this typically leads to myocardial ischema. Percutaneous transluminal coronary angioplasty (PTCA), i.e., the insertion and inflation of a balloon catheter into a stenotic vessel to affect its repair, is widely accepted as an option in the treatment of obstructive coronary artery disease. Other vascular invasive therapies include antherectomy (mechanical systems to remove plaque residing inside an artery), laser ablative therapy, and the like. However, restenosis at the site of a prior invasive coronary artery disease therapy occurs in a majority of cases. Restenosis, defined angiographically, is the recurrence of a 50% or greater narrowing of a luminal diameter at the site of a prior coronary artery disease therapy, such as a balloon dilatation in the case of PTCA therapy. Restenosis is a major problem that limits the long-term efficacy of invasive coronary disease therapies. In particular, an intra-luminal component of restenosis develops near the end of the healing process initiated by vascular injury, which then contributes to the narrowing of the luminal diameter. This phenomenon is sometimes referred to as "intimal hyperplasia." In some instances, restenosis develops so rapidly that it may be considered a form of accelerated atherosclerosis induced by injury. Additionally, the rapid onset of restenosis is compounded by the lack of predictability to determine which patients, vessels, or lesions will undergo restenosis.

Although the mechanism of restenosis is not fully understood, clinical evidence suggests that restenosis results from a migration and rapid proliferation of a subset of predominately medially derived smooth muscle cells, which is apparently induced by the injury caused by the invasive therapy. Such injury, for example, is caused by the angioplasty procedure when the balloon catheter is inflated and exerts pressure against the artery wall, resulting in medial tearing. It is known that smooth muscle cells proliferate in response to mechanical stretch and stimulation by a variety of growth factors. It is believed that such proliferation stops one to two months after the initial invasive therapy procedure but that these cells continue to express an extracellular matrix of collagen, elastin, and proteoglycans. Additionally, animal studies have shown that after balloon injury, denudation of endothelial cells occurs, followed by platelet adhesion and aggregation, and the release of platelet-derived growth factor (PDGF) as well as other growth factors. As mentioned above, this mass of tissue contributes in the re-narrowing of the vascular lumen in patients who have restenosis. It is believed that a variety of biologic factors are involved in restenosis, such as the extent of the injury, platelets, inflammatory cells, growth factors, cytokines, endothelial cells, smooth muscle cells, and extracellular matrix production, to name a few.

Attempts to inhibit or diminish restenosis include administration of pharmacological agents, such as aspirin, antiplatelet drugs, anticoagulants, corticosteroids, calcium-channel blocker, fish oils, and the like, all of which have demonstrated limited success. Other solutions include providing a stent coated with an anti-thrombogenic agent that may reduce platelet and fibrin deposition (U.S. Pat. No. 4,768,507 to Fischell et al.) or providing a stent including fibrin and an elutable drug capable of providing treatment of restenosis (U.S. Pat. No. 5,591,227 to Dinh et al.). Still other methods to diminish restenosis include the delivery of modified viruses, especially adenoviruses, that carry gene sequences capable of ameliorating or preventing the symptoms of cardiovascular disease, such as that described in International Publication No. WO 94/27612 (French et al.).

In searching for alternative therapies that may decrease the likelihood of restenosis, gamma radiation has been shown to limit cell proliferation by arresting cell division thereby reducing the number of clonal progenitors. However, re-injury or other stimuli can induce a response by smooth muscle cells by migration, proliferation and matrix synthesis, as mentioned above. Ionizing radiation has been shown to inhibit thymidine uptake and collagen synthesis by cultured fibroblasts. For example, it has been shown that low doses of superficial x-rays after surgery may prevent hypertrophic scarring and keloid formation that typically results from the excessive formation of collagen after surgical injury. Thus, radiation may inhibit cellular hyperplasia by either killing progenitor cells or limiting their replication.

SUMMARY OF THE INVENTION

What is yet needed is an implantable device capable of reducing the occurrence of restenosis, for example by reducing inflammation, with or without delivering therapeutic drugs to the in vivo treatment site.

This invention relates to an implantable device capable of reducing restenosis. Preferably, the implantable device according to the invention is biodegradable once implanted in a body lumen to treat or prevent injury. The term "injury" means a trauma, which may be incidental to surgery or other treatment methods including deployment of a stent, or a biologic disease, such as an immune response or cell proliferation caused by the administration of growth factors. In addition, the methods of the invention may be performed in anticipation of "injury" as a prophylactic. A prophylactic treatment is one that is provided in advance of any symptom of injury in order to prevent injury, prevent progression of injury or attenuate any subsequent onset of a symptom of such injury.

In accordance with the invention, an implantable device includes a structure including a polyamino acid component. The polyamino acid component includes L-arginine, and preferably consists essentially of two different amino acids, one of which is L-arginine. The polyamino acid component may form a film or a coating on at least a portion of the structure or the polyamino acid component may form an integral portion of the structure.

In another embodiment, the polyamino acid component of the structure includes a mixture of polyamino acids. The mixture, which may be a polymer blend, includes at least one polyamino acid that includes, and preferably consists essentially of, L-arginine and one other amino acid, and at least one polyamino acid that includes, and preferably consists essentially of, two amino acids other than L-arginine.

The structure of the device preferably includes a shape which is capable of minimizing restenosis in an internal human body site, such as an artery, vein, urethra, other body lumens, cavities, and the like. In one embodiment, the shape is preferably generally cylindrical, and more preferably, the shape is selected from the group of a catheter, a stent, and a guide wire. In another embodiment, the shape is preferably generally sheet-like.

DETAILED DESCRIPTION OF THE INVENTION

The present invention provides an implantable device including a structure that includes a polyamino acid component. The polyamino acid component includes at least L-arginine, and preferably, only one other amino acid. Preferably, the structure includes a shape capable of minimizing restenosis in an internal human body site. In one embodiment, the shape is preferably generally cylindrical, more preferably the shape is selected from the group of a catheter, a stent, and a guide wire. In another embodiment, the shape is preferably generally sheet-like.

One more preferred shape is a stent that is a particularly useful shape in artery/vascular therapies. The term "stent" refers to any device capable of being delivered by a catheter and which, when placed into contact with a portion of a wall of a lumen to be treated, will also provide support to the lumen wall. A stent typically includes a lumen well-contacting surface and a lumen-exposed surface. Where the stent is shaped generally cylindrical or tube-like, including a discontinuous tube or ring-like structure, the lumen-wall contacting surface is the surface in close proximity to the lumen wall whereas the lumen-exposed surface is the inner surface of the cylindrical stent.

The stent (or other implantable devices according to the present invention) can include polymeric or metallic elements, or combinations thereof, onto which a polyamino acid component is applied. For example, a deformable metal wire stent is useful as a stent framework of this invention, such as that described in U.S. Pat. No. 4,886,062 to Wiktor, which discloses preferred methods for making a wire stent. Other metallic stents useful in this invention include those of U.S. Pat. No. 4,733,655 to Palmaz and U.S. Pat. No. 4,800,882 to Gianturco. Polymers, preferably, nonbioabsorbable polymers, can be used as alternatives to metallic stents. For example, another stent suitable for this invention includes the self-expanding stent of resilient polymeric material as disclosed in International Publication No. WO 91/12779.

The stents (or other implantable devices according to the present invention) of this invention should not substantially induce inflammatory and neointimal responses. Examples of biostable nonabsorbable polymers that have been used for stent construction with or without metallic elements include polyethylene terephthalate (PET), polyurethane urea, and silicone (for example, see van Beusekom et al. *Circulation* 86(supp. I):1–731, 1992 and Lincoff et al. *J. Am. Coll Cardio* 21(supp. 1): 335A, 1994. Accordingly, a stent (or other implantable device structure) may be formed from a material selected from the group of a metal, silicone, polyurethane, polysulfone, cellulose, polyethylene, polypropylene, a polyamide, polyester, polytetrafluoroethylene, and various combinations (including copolymers, terpolymers, etc., and mixtures) of two or more of these materials.

Figure 1:
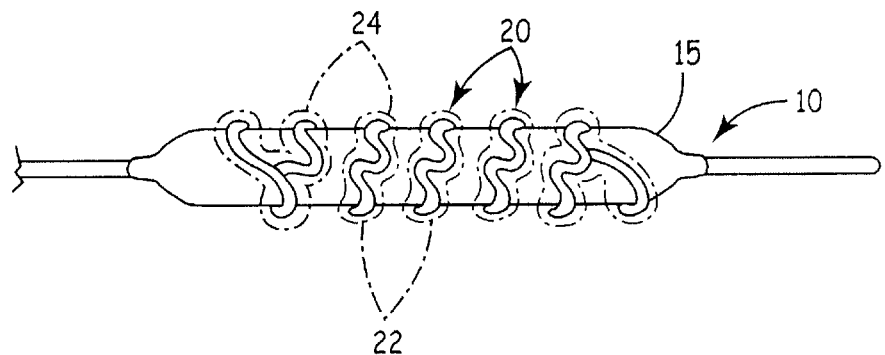
FIG. 1 is an elevational view of one embodiment of a device according to the invention with a balloon catheter as a mode of delivery of the device.

Referring now to FIG. 1, a stent is shown in place on a balloon catheter. A catheter 10 has a balloon 15 upon which a stent 20 has been placed. The stent 20 preferably comprises a framework 22 and a polyamino acid coating 24 thereon. The stent framework 22 is deformable and can be formed from a polymeric material, a metal, or a combination thereof. The balloon 15 is positioned in FIG. 1 adjacent the lumen-exposed surface of the stent to facilitate delivery of the stent. The stent 20 can be modified to increase or to decrease the number of framework members provided per centimeter in the stent framework 22. Similarly, the number of framework members turns per centimeter can also be modified to produce a stiffer or a more flexible stent framework. Although the polyamino acid component is shown as a coating 24, it is to be understood that, for the purposes of this invention, the polyamino acid component can be incorporated into the material of the stent, particularly if the stent is made of a polymeric material.

The polyamino acid coating 24 can be applied to a stent framework by simply immersing the stent framework into a solution containing a polyamino acid composition or by spraying the solution onto the stent framework and allowing the composition to dry to form a polyamino acid coating. The overall coating should be thin enough so that it will not significantly increase the profile of the stent for intravascular delivery by a catheter. For example, the coating thickness is less than about 0.005 cm, more preferably less than about 0.003 cm.

Figure 2:
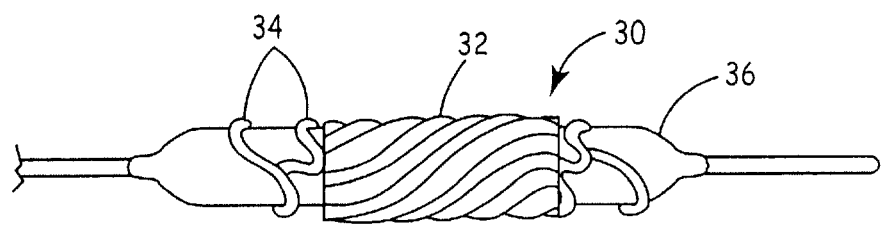
FIG. 2 is an elevational view of another embodiment of a device according to the invention with a balloon catheter as a mode of delivery of the device.

Referring to FIG. 2, an alternative stent 30 is shown. The stent framework 34 is affixed with a polyamino acid film 32. This can be accomplished by wrapping the film 32 around the stent framework 34 and securing the film 32 to the framework 34 (i.e., the film is usually sufficiently tacky to adhere itself to the framework but a medical grade adhesive could also be used if needed) so that the film 32 will stay on the balloon 36 and framework 34 until it is delivered to the site of treatment. The film 32 is preferably wrapped over the framework with folds or wrinkles that will allow the stent 30 to be readily expanded into contact with the wall of the lumen to be treated. Preferably, the film 32 is located on a lumen-wall contacting surface 33 of the stent framework 34 for a substantially uniform contact between the polyamino acid film 32 and a lumen wall, for example, an arterial wall membrane (not shown).

The polyamino acid film 32 can be applied to the stent framework as a polyamino acid network typically in a sheet format. For example, the sheet format may be formed from a polyamino acid component having sufficient mechanical and rheological properties so that it can exist as an unsupported substantially continuous sheet that can be attached to the stent as indicated above.

Figure 3:
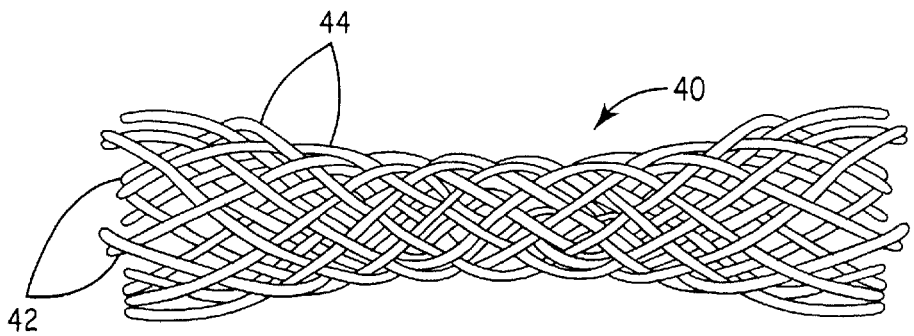
FIG. 3 is an elevational view of another embodiment of a device according to the invention.

Referring to FIG. 3, a stent is shown that has a first set of filaments 42 that are helically wound in a second direction. Either or both set of filaments that are helically wound in a second direction. Either or both set of filaments can include a polyamino acid component. The polyamino acid component should have sufficient mechanical and rheological properties so that it can exist as a filament that can then be woven or braided to form the stent.

Thus, in one embodiment of the present invention, the polyamino acid component is a coating on at least a portion of the structure. In another embodiment, the polyamino acid component is an integral portion of the structure. In yet another embodiment, the polyamino acid component is a film on at least a portion of the structure. In still another embodiment, the polyamino acid component forms filaments on at least a portion of the structure. Thus, the polyamino acid component can be in a wide variety of forms in or on the structure of a device.

Polyamino Acid Component

As mentioned above, an implantable device according to the present invention is generally a structure including a polyamino acid component, wherein the polyamino acid component includes at least L-arginine. Other suitable amino acids include those that are naturally occurring or synthetically derived. Preferably, the polyamino acid component is water insoluble.

The polyamino acid component includes a plurality of amino acids, at least one of which is L-arginine, so long as the resulting polyamino acid component does not elicit an adverse reaction (e.g., an immunological response) in vivo once implanted. "Plurality" is intended to refer to a polyamino acid network that includes more than one amino acid in the network, although each amino acid in the network may be the same amino acid. Preferably, the polyamino acid network includes, more preferably consists essentially of, two amino acids, one of which is L-arginine.

Suitable polyamino acids can be formed by known techniques. For example, U.S. Pat. No. 5,646,239 (Constancis et al.) describes the formation of polyamino acids by condensation of a dicarboxylic acid with a sulfur-containing amino acid or one of its derivatives so that disulfide bridges are formed in the resulting polymer. Additionally, U.S. Pat. No. 5,780,579 (Soula et al.) describes the preparation of polyamino acids by polymerization of N-carboxyanhydrides of at least one amino acid. As described above, the polyamino acid component can be, for example, in the form of a coating, a film, and/or integral part of the medical device itself. It is also within the scope of the present invention that the polyamino acid component itself may be biodegradable in that it diffuses or absorbs in biological tissues.

The polyamino acid component of the devices of the present invention (e.g., any of the coatings, films, and filaments described above) can include one polyamino acid containing at least L-arginine. Alternatively, it can include a mixture (e.g., a polymer blend) of different polyamino acids, each containing at least L-arginine. In another embodiment, the polyamino and acid component of the devices of the present invention can include a mixture of one or more polyamino acids, at least one of which contains at least L-arginine. In yet another embodiment, it can include a mixture of one or more polyamino acids, at least one of which contains at least L-arginine, with one or more polymers other than a polyamino acid. Suitable polymers with which the polyamino acid can be combined can be either biostable or biodegradable. In yet other embodiments, the structure may contain a separate coating, film, filament, etc., of a polymer or mixture of polymers other than polyamino acids. Examples of polymers other than polyamino acids include a silicone, a polyurethane, a polysulfone, a polyolefin (e.g., polyethylene or polypropylene), a non-polyamino acid polyamide, a polysaccharide (e.g., starch, cellulose, chitosan, dextran, or mucopolysaccharides such as hyaluronic acid or chondroitin sulfate), a protein (e.g., collagen, gelatin, albumin, or globulin), a polyester (e.g., lactic and/or glycolic polyester), a polyorthoester, a polyanhydride, or polyphosphazene, and various combinations (including copolymers, terpolymers, etc., and mixtures) thereof.

Therapeutic Substance

A variety of therapeutic substances can be included in a medical device according to the present invention. The therapeutic substance may be incorporated into a device in a wide variety of ways, such as in the polyamino acid component. Preferably, it is incorporated into or on the structure as a mixture or otherwise in combination with one or more of the polymers (typically, those other than polyamino acids) described above. For example, the therapeutic substrate can be incorporated into or on a polymeric sheet by dipping, spraying, and/or brushing a solution containing a therapeutic substance and allowing it to dry.

Preferable therapeutic substances are those that are thought to be useful in the treatment of restenosis, for example those described in published international patent application WO 91/12779 entitled "Intraluminal Drug Eluting Prosthesis." Examples of suitable therapeutic substances include glucocorticoids (e.g., dexamethasone, betamethasone), heparin, hirudin, tocopherol, angiopeptin, aspirin, ACE inhibitors, growth factors, oligonucleotides, antiplatelet agents, anticoagulant agents, antimitotic agents, antioxidants, antimetabolite agents, anti-inflammatory agents, and combinations thereof. Further, other vasoreactive agents such as nitric oxide releasing agents could also be used. The amount and desired release rate of such therapeutic substances can be readily controlled by one of skill in the art.

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

What is claimed is:

1. An implantable device comprising a structure comprising a polyamino acid component comprising L-arginine.

2. The implantable device of claim 1 wherein the polyamino acid component comprises a polyamino acid consisting essentially of L-arginine and one other amino acid.

3. The implantable device of claim 2 wherein the polyamino acid component forms a film on at least a portion of the structure.

4. The implantable device of claim 2 wherein the polyamino acid component forms a coating on at least a portion of the structure.

5. The implantable device of claim 2 wherein the polyamino acid component forms an integral portion of the structure.

6. The implantable device of claim 1 wherein the polyamino acid component is water insoluble.

7. The implantable device of claim 1 wherein the structure comprises a generally cylindrical shape.

8. The implantable device of claim 7 wherein the shape is selected from the group of a catheter, a stent, and a guide wire.

9. The implantable device of claim 8 wherein the structure is formed from a material selected from the group of a metal, silicone, polyurethane, polysulfone, cellulose, polyethylene, polypropylene, polyamide, polyester, polytetrafluoroethylene, and a combination of two or more of these materials.

10. The implantable device of claim 1 wherein the polyamino acid component further comprises a polymer selected from the group of a silicone, a polyurethane, a polysulfone, a polyolefin, a non-polyamino acid polyamide, a polysaccharide, a protein, a polyester, a polyorthoester, a polyanhydride, or polyphosphazene, and a combination of two or more of these polymers.

11. The implantable device of claim 1 wherein the structure further comprises a polymer selected from the group of a silicone, a polyurethane, a polysulfone, a polyolefin, a non-polyamino acid polyamide, a polysaccharide, a protein, a polyester, a polyorthoester, a polyanhydride, or polyphosphazene, and a combination of two or more of these polymers.

12. The implantable device of claim 11 wherein the structure further comprises a therapeutic substance.

13. The implantable device of claim 12 wherein the therapeutic substance is selected from the group of glucocorticoids, heparin, hirudin, tocopherol, angiopeptin, aspirin, ACE inhibitors, growth factors, oligonucleotides, antiplatelet agents, anticoagulant agents, antimitotic agents, antioxidants, antimetabolite agents, anti-inflammatory agents, and a combination of two or more of these substances.

14. The implantable device of claim 1 wherein the polyamino acid component comprises a polyamino acid comprising L-arginine and at least one other amino acid, and a polyamino acid comprising at least two amino acids other than L-arginine, wherein the polyamino acid component does not elicit an adverse reaction in vivo.

15. An implantable device comprising a structure comprising a polyamino acid component comprising a mixture of polyamino acids, wherein the mixture comprises at least one polyamino acid consisting essentially of L-arginine and one other amino acid, and at least one polyamino acid consisting essentially of two amino acids other than L-arginine.

16. The implantable device of claim 15 wherein the mixture of polyamino acids forms a coating on at least a portion of the structure.

17. The implantable device of claim 15 wherein the structure is in the form of a catheter, a stent, or a guide wire.

18. The implantable device of claim 15 wherein the structure is formed from a material selected from the group of a metal, silicone, polyurethane, polysulfone, cellulose, polyethylene, polypropylene, polyamide, polyester, polytetrafluoroethylene, and a combination of two or more of these materials.

19. The implantable device of claim 15 wherein the polyamino acid component further comprises a polymer selected from the group of a silicone, a polyurethane, a polysulfone, a polyolefin, a non-polyamino acid polyamide, a polysaccharide, a protein, a polyester, a polyorthoester, a polyanhydride, or polyphosphazene, and a combination of two or more of these polymers.

20. The implantable device of claim 19 wherein the polyamino acid component further comprises a therapeutic substance.

* * * * *

UNITED STATES PATENT AND TRADEMARK OFFICE
CERTIFICATE OF CORRECTION

PATENT NO.     : 6,746,481 B1
DATED          : June 8, 2004
INVENTOR(S)    : Vincent Larik et al.

It is certified that error appears in the above-identified patent and that said Letters Patent is hereby corrected as shown below:

Title page,
Item [54], Title, delete "IMPLATABLE" and insert -- IMPLANTABLE --.

Signed and Sealed this

Twenty-third Day of May, 2006

JON W. DUDAS
*Director of the United States Patent and Trademark Office*